United States Patent [19]

Rhim et al.

[11] Patent Number: 4,981,625

[45] Date of Patent: Jan. 1, 1991

[54] MONODISPERSE, POLYMERIC MICROSPHERES PRODUCED BY IRRADIATION OF SLOWLY THAWING FROZEN DROPS

[75] Inventors: Won-Kyu Rhim, Pasadena; Michael T. Hyson, Glendale; Sang-Kun Chung, Diamond Bar; Michael S. Colvin, Malibu; Manchium Chang, Los Angeles, all of Calif.

[73] Assignee: California Institute of Technology, Pasadena, Calif.

[21] Appl. No.: 167,877

[22] Filed: Mar. 14, 1988

[51] Int. Cl.[5] .......................... B28B 9/10; B29C 35/00
[52] U.S. Cl. .......................................... 264/13; 264/5;
264/10; 522/5; 425/5; 425/6; 428/402;
526/909; 523/223
[58] Field of Search ...................... 427/213.33, 213.34;
264/4.3, 4.33, 4.7, 5, 10, 13; 526/909; 428/407,
402; 523/223; 522/5, 71

[56] References Cited

U.S. PATENT DOCUMENTS

| | | | |
|---|---|---|---|
| 3,427,250 | 2/1969 | Haas | 264/4.7 X |
| 3,976,629 | 8/1976 | Hayward et al. | 526/909 X |
| 4,123,396 | 10/1978 | Rembaum et al. | 428/407 X |
| 4,162,282 | 7/1979 | Fulwyler et al. | 264/9 |
| 4,170,685 | 10/1979 | Rembaum et al. | 428/407 X |
| 4,247,434 | 1/1981 | Vanderhoff et al. | 523/223 X |
| 4,438,239 | 3/1984 | Rembaum et al. | 428/407 X |
| 4,459,378 | 7/1984 | Ugelstad | 523/205 |
| 4,552,812 | 11/1985 | Margel et al. | 428/407 |
| 4,553,917 | 11/1985 | Lee | 264/23 X |
| 4,623,706 | 11/1986 | Timm et al. | 526/918 X |
| 4,707,523 | 11/1987 | Chang et al. | 525/372 |
| 4,774,265 | 9/1988 | Ugelstad | 521/55 |
| 4,791,182 | 12/1988 | Vanderhoff et al. | 524/458 |
| 4,795,330 | 1/1989 | Noakes et al. | 425/6 |
| 4,929,400 | 5/1990 | Rembaum et al. | 264/10 |

FOREIGN PATENT DOCUMENTS

| | | | |
|---|---|---|---|
| 112321 | 7/1982 | Japan | 522/5 |
| 439159 | 12/1974 | U.S.S.R. | 522/5 |

OTHER PUBLICATIONS

*Chemical Abstracts*, vol. 74, No. 8, Abstract No. 37349z, Bowman, R. A., Formation of . . . Microspheres by Freeze Form Vacuum-Dry, 1970.
Rhim et al., "Technical Support Package on Making Polymeric Microspheres", Nasa Tech. Brief, v. 13, No. 9, Item 85, p. 98, NPO-17023, Sep. 1989.
W. K. Rhim et al., "Containerless Polymeric Microsphere Production for Biomedical Applications", Mat. Res. Soc. Sump. Proc., vol. 87, 1987.
J. W. Vanderhoff et al., Proc. Am. Chem. Soc., Div. Polym. Sci.: Sci. & Eng., New York Meeting, 54, 587, 1986.
J. Ugelstad, Proc. Am. Chem. Soc., Div. Polym. Sci. & Eng., New York Meeting, 54, 521, 1986.
R. E. Bater, Biomat. Med. Dev. Art Org. 12 (3–4), 133–159, 1984–85.
Manchium Chang, et al., Proc. Am. Chem. Soc., Div. Polym. Sci.: Sci. & Eng., New York Meeting, 54, 526, 1986.
Alan Rembaum et al., Macromolecules 9, 328, 1976.
Michael Colvin et al., Microspheres: Medical and Biological Applications, edited by A. Rembaum and Zoltan Tokes, (CRC Press, [in press]).

*Primary Examiner*—Richard D. Lovering
*Assistant Examiner*—John M. Covert
*Attorney, Agent, or Firm*—Marvin E. Jacobs

[57] ABSTRACT

Monodisperse, polymeric microspheres are formed by injecting uniformly shaped droplets of radiation polymerizable monomers, preferably a biocompatible monomer, having covalent binding sites such as hydroxyethylmethacrylate, into a zone, impressing a like charge on the droplet so that they mutually repel each other, spheroidizing the droplets within the zone and collecting the droplets in a pool of cryogenic liquid. As the droplets enter the liquid, they freeze into solid, glassy microspheres, which vaporizes a portion of the cryogenic liquid to form a layer. The like-charged microspheres, suspended within the layer, move to the edge of the vessel holding the pool, are discharged, fall and are collected. The collected microspheres are irradiated while frozen in the cryogenic liquid to form latent free radicals. The frozen microspheres are then slowly thawed to activate the free radicals which polymerize the monomer to form evenly-sized, evenly-shaped, monodisperse polymeric microspheres.

20 Claims, 1 Drawing Sheet

U.S. Patent        Jan. 1, 1991        4,981,625
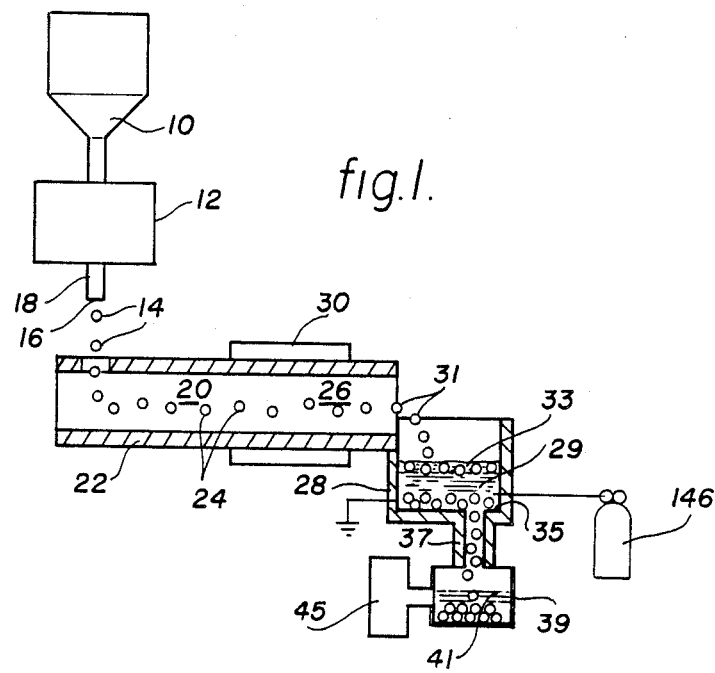
fig.1.
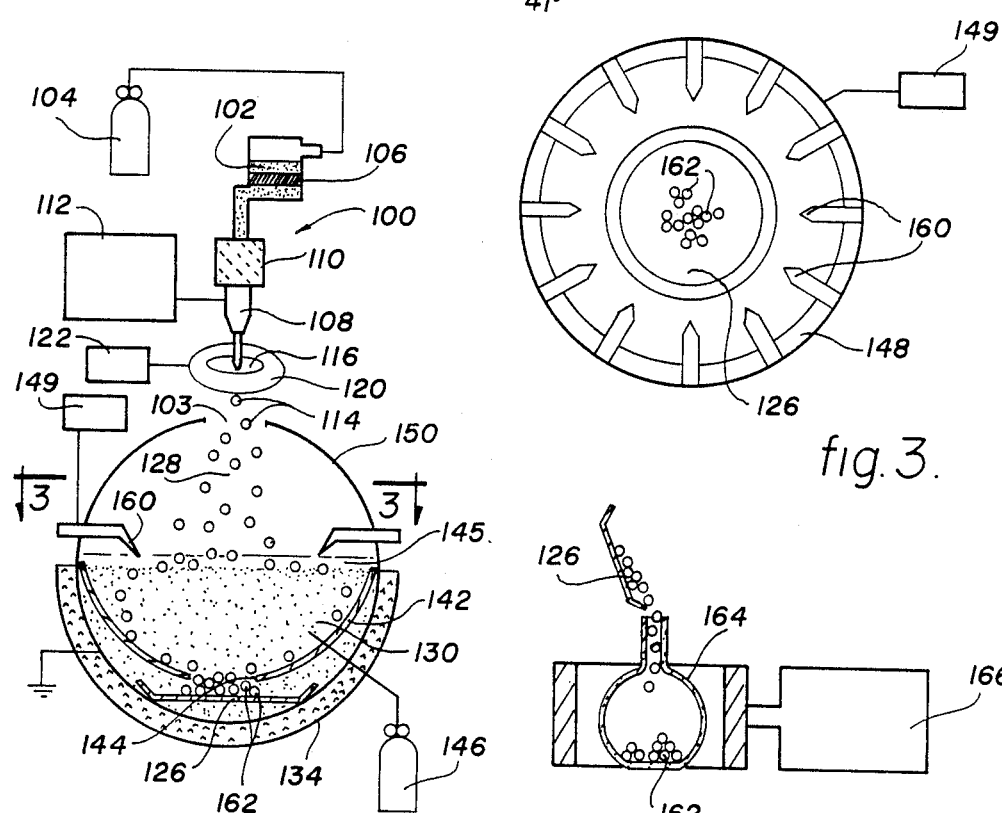
fig.2a.
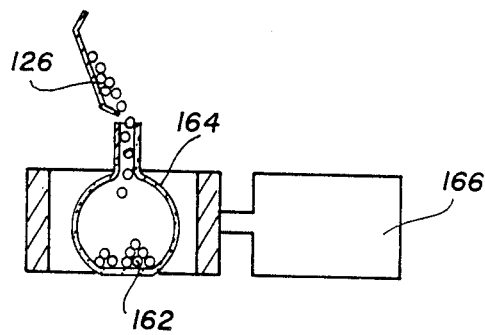
fig.3.
fig.2b.

MONODISPERSE, POLYMERIC MICROSPHERES PRODUCED BY IRRADIATION OF SLOWLY THAWING FROZEN DROPS

ORIGIN OF THE INVENTION

The invention described herein was made in the performance of work under a NASA contract, and is subject to the provisions of Public Law 96-517 (35 USC 202) in which the contractor has elected to retain title.

TECHNICAL FIELD

The present invention relates to a process for the production of polymeric particles and, more particularly, this invention relates to a containerless process for the mass production of evenly-sized, monodispersed magnetic or non-magnetic, microspheres by the polymerization of slowly thawing, uniformly-sized and shaped, frozen droplets produced by spraying liquid monomer through a cryogenic zone.

BACKGROUND OF THE INVENTION

There are extensive biological, medical and industrial uses for small polymeric particles having uniform size and even more extensive uses for magnetic polymeric microspheres. Small polymeric microspheres, especially those containing covalent binding functional groups, are finding increasing uses in separation processes such as affinity chromatography, in labelling and sorting of biological cells, in diagnostic testing and in clinical treatment. Metal and metal oxide containing microspheres, particularly those containing magnetically susceptible materials, find use in catalysis and electron microscopy. Uniformly-sized particles can be utilized to calibrate instruments or filters and the like.

Magnetic particles also find use in biology as substrates or carriers for enzymes or proteins and in cell biology as substrates derivatized with ligands capable of labelling specific cells. The labelled cells can then be separated from a mixture containing both labelled and unlabelled cells or from mixtures of labelled cells with other proteinaceous material. Magnetic microspheres can also be utilized to deliver a pharmaceutical to a specified location or organ in an animal or person.

Large, uniform, biocompatible particles are needed for chromatography, affinity chromatography and cell separation procedures.

A chromatography column is made by packing a slurry of small particles into a tube to form a filter bed. Channels for liquid flow form between the particles. Columns are widely used to separate chemical mixtures, proteins or cell populations. Cells or proteins with different affinities for the packing are more or less retarded in their flow and become separated into bands as they flow through the column. If very similar compounds can be separated, the column has high resolution. When packing particles differ in size, smaller particles can clog many of the larger channels and lower flow rate. With a distribution of channel sizes, parts of the mixture flow faster through larger channels into adjacent bands, lowering the column's resolution. Uniform particles forming homogeneous packings give the highest resolution and flow rates because channel size and flow rate are everywhere the same. Hence the quest for uniform particles.

The higher the surface area, the shorter the column necessary to effect a separation. Therefore, particles near 10 $\mu$m diameter are typically used for chemical separations. Small particles give slower flow rates, higher pressures and the column may clog, but this is justified for analytic preparations. For industrial scale separations, larger particles (50–100 $\mu$ dia.) are less troublesome. For separating cells, uniform, biocompatible particles, 100–300 $\mu$ dia. form channels large enough that cells can flow freely. Otherwise, cells can become trapped or damaged.

Research and medical procedures often need pure cell populations. Cells are usually too similar to be separated by simple physical properties, like density, but their surface chemistry is often unique. Monoclonal antibodies can be made that bind only to a single cell type, but we have few ways of using them for cell separations. Fluorescence activated cell sorters (FACS) are slow, have fairly low accuracy, and a high cost; panning is inefficient; and harvesting viable cells from antibody-coated netting, strings or tubes is difficult. An affinity chromatography column, with cell-specific antibodies conjugated to its packing, can separate cells. Ideally, it should have no affinity for any other kind of cell. Such non-specific binding is less important in cell depletions, where cells to be removed are adsorbed on the packing. In positive selection, however, desired cells are bound to the packing. Any non-specific adsorption lessens the accuracy of separation. Biocompatible materials with low non-specific binding are needed.

LIST OF CITED REFERENCES

1. J. W. Vanderhoff et al., Proc. Am. Chem. Soc., Div. Polym. Sci.: Sci. & Eng., New York Meeting, 54 587, 1986.
2. J. Ugelstad, Proc. Am. Chem. Soc., Div. Polym Sci.: Sci. & Eng., New York Meeting, 54, 521, 1986.
3. R. E. Bater, Biomat. Med. Dev. Art. Org. 12 (3–4), 133–159, 1984–85.
4. Manchium Chang, et al., Proc. Am. Chem. Soc., Div. Polym. Sci.: & Eng., New York Meeting, 54, 526, 1986.
5. Alan Rembaum, et al., Macromolecules 9, 328, 1976.
6. Michael Colvin, et al., Microspheres: Medical and Biological Applications, edited by Alan Rembaum and Zoltan Tokes, (CRC Press, [in press]).

STATEMENT OF THE PRIOR ART

Current methods producing the most uniform particles: suspension or emulsion polymerization, or emulsion polymerization combined with swelling, cannot make particles much larger than 100 $\mu$ diameter. Currently, the range of sizes and materials used as well as the size, quantity, and uniformity of particles produced is limited by a number of factors. Typically in suspension polymerization, monomer, with dissolved free radical initiator, is suspended in an immiscible reactive media, stirred to break it into drops and heated to cause polymerization. This yields non-uniform particles in the 50–400 $\mu$m range. Physical stirring to distribute the drops through a host liquid causes many of the drops to break, and other drops tend to coalesce due to the stirring. Such microsphere product having a wide size distribution is undesirable for many applications. In suspension polymerization, the monomer and the host medium must be immiscible in each other, which in turn imposes strict limitations on the choice of monomer-host combinations. For many useful monomers, there has not been a suitable host liquid to carry out the sphere-forming suspension polymerization process.

Narrower distributions are obtained by sieving. In emulsion polymerization, monomers are emulsified with surfactant to form micelles in an immiscible reactive media and are polymerized by heat or radiation. During polymerization, the particles grow at a rate limited by diffusion of reactants at their surface. Therefore, small particles, with a higher surface/volume ratio, grow more rapidly than large ones. This self-regulating process tends to make uniform particles, but of only up to 1 μ diameter. The particles can be left with unwanted surfactants adsorbed on their surface.

For larger particles, the 1 μ seeds are swollen with more fresh monomer and reacted again. The swollen particles are sticky and can grow too large to be colloidal. In gravity, they settle out and coalesce. Stirring helps, but particles can become distorted or collide. Vanderhoff [1] starts with 1 μ seed particles with the coefficient of variation (a ratio of the standard deviation of particle diameter to the mean particle diameter) or CV of 1.36%. He then swells and polymerizes them in microgravity. Several repetitions gave 30 μ particles with a 1.35% CV. On average, microgravity improved particle CV from 2.94 to 1.37%. Ugelstad has reported a similar CV for 100 μ particles [2]. However, as particle size increases, the emulsions become less stable and predictable, resulting in a coagulated polymer, not particles. Making uniform particles larger than 50 μ is difficult and a 100 μ diameter is near the upper size limit.

Any material which contacts living tissue may be toxic and cause denaturation of proteins, clotting, or non-specific binding. A substance causing few effects is biocompatible. While the determinants of non-specific binding and biocompatibility are complex, some basic principles are clear. Hydrophilic polymers generally bind less to proteins or cells. Negatively charged surfaces repel the negative surfaces of living cells and bind less than positively charged ones. A low surface tension (about 22 dynes/cm$^2$) reduces binding [3].

Most of the prior methods are incapable of producing uniformly sized or shaped spherical particles. The particles are somewhat ovoid in shape and are produced in a range of sizes. The magnetic oxide content also varies considerably. In some methods the magnetic oxide is present only on the surface of the polymeric particles.

A few types of monodisperse polymeric particles can be produced by current techniques. The particles that are available are very expensive. Some very uniform particles produced in space by Vanderhoff are being sold by the U.S. Bureau of Standards for $500,000 per gram. Monodisperse polymer particles can not be produced from most types of monomers by the methods presently utilized.

Only a complicated process, stepwise seed growth emulsion polymerization, produces large polymer microspheres of nearly uniform size above 2 microns. This method is very lengthy, leaves unwanted impurities in the final product and can only be used with a few materials or monomers—all of which are hydrophobic. The microspheres must be washed and freeze-dried to obtain a dry product.

STATEMENT OF THE INVENTION

Very small, individual polymeric microspheres with very precise size and a wide variety of properties can be produced in accordance with the present invention. Very pure, monodisperse particles can be produced from a wide variety of monomers, including hydrophilic monomers as well as many substances which can be sprayed in a liquid form, such as polymers, proteins, waxes, starches and even glasses and metals. The particles can be produced in a wide range of particle sizes, densities and morphologies. The polymer particles can be solid, hollow or can encapsulate a second material. Many types of fillers can be incorporated into the particles, e.g., magnetic fillers such as magnetite. The fillers are distributed in the volume of the particles rather than on the surface as provided by some of the prior methods of producing magnetic, polymeric particles. The microsphere particles can contain covalent functional groups on the surface capable of further reaction with and attachment to other materials such as fluorescent dyes, antibodies or other proteins. Macroreticular particles can also be made using the present invention simply by incorporation of a non-reactive diluent with the monomers.

The microspheres are produced in accordance with the invention in a simple process. Uniformly-sized droplets of polymerizable liquid are formed in an injector device. The droplets are injected into a containerless environment and assume a uniform spheroid shape as they fall or travel through the environment. The spheroid droplets are frozen as they pass through the environment or as they are collected in a pool of cryogenic liquid. The frozen microspheres are then irradiated to create latent free radicals within the particles. The microspheres are then polymerized while slowly thawing the microspheres to activate the free radicals. Polymeric microspheres, having precise size range with diameters varying no more than plus or minus 5 percent, usually plus or minus 1 percent from an average size, are recovered. The microspheres have a C.V. below 5, preferably less than 2.0.

The method is applicable to any monomer that can be provided in liquid form. The monomer can be hydrophobic or hydrophilic. The bulk monomer can be a liquid at ambient temperature or can be dissolved in solvent. The monomer can also be a solid which is heated before and after being fed to the injector in order to convert the solid material to a liquid. Fillers can be predispersed in the liquid monomer to form a uniform dispersion before the liquid is formed into droplets. The process of the invention can be conducted without solvent, catalyst, suspending agents, emulsifiers or other reactants providing a very pure particle directly and avoiding costly post-polymerization purification techniques. Purity is further enhanced by the containerless environment in which the particle is exposed during polymerization to a gaseous, vacuum or near vacuum atmosphere containing very few molecules. The very pure environment prevents contamination by extraneous impurities that could be present in a liquid polymerization media or impurities provided by the container itself that can be carried into solution. The use of radiation induced polymerization also eliminates the introduction of impurities provided by residues of catalysts, initiators or suspending agents utilized in emulsion polymerization.

Fluid dynamic forces cause the liquid droplet to assume a spherical shape. Freezing the liquid sphere while spherical results in the maintenance of the spherical shape throughout further processing. In contrast, the forces in a stirred, liquid emulsion tend to produce egg-shaped polymeric beads. Radiation-induced polymerization converts the liquid droplets into a solid sphere with the expenditure of little energy. The final product is produced in a form ready for use.

The evenness of the size of the microspheres is due, in large part, to the injection of evenly sized drops into the polymerizing environment. A wide variety of sizes, including large sizes, can be produced since larger drops of higher density can readily be levitated or dropped through the environment until the drop is frozen. The levitation or drop techniques are not sensitive to the ionic or surface characteristics of the droplet and hydrophilic or hydrophobic monomers can readily be polymerized greatly increasing the range and type of materials available in monodisperse form. The internal dispersion of the magnetic or other filler reserves the functional sites on the surface. The surface is in a more biocompatible form and in a form more available for attachment to proteins, dyes or other subtrates.

The monodisperse polymeric microspheres produced in the method of the invention have many uses. The microspheres can be used in polymeric magnetic separation of cancer cells or in labelling and visualization of cellular structures. The particles can be used for column packing material for liquid chromatography as well as affinity chromatography. The uniformity of size and shape are major factors in the column efficiency obtained. The microsphere particles have high surface area and can be made porous, like sponges, a form in which they are useful as catalysts or catalyst supports. The pure hydrophilic materials have a low non-specific absorption of hydrophilic materials such as proteins. Their large, uniform size coupled with mechanical strength allows high flow rates and high pressures to be used without breaking the particles. Materials stable in strong acids and bases can be made, allowing their use in a wide range of conditions. Also, if a catalyst were carried on the surface of a magnetic particle, the catalyst particle could be magnetically recovered after the reaction was completed. Further, by adding various metals, such as platinum, the particles themselves could be rendered catalytic. The magnetic particles are electron dense and therefore could be used to visualize biological or other structures in an electron microscope without the necessity to coat the particle with gold. Instruments, filters and the like can be calibrated using the very uniform, particles produced in the invention. New forms of paint or metal coatings for data storage can be fabricated using microsphere particles produced by the invention. The microspheres will also find use in diagnosis, therapy and drug targeting.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 1 is a schematic view of a general system for producing monodisperse, polymeric microspheres according to the invention;

FIGS. 2A and 2B are views in elevation of a monodisperse microsphere producing apparatus; and FIG. 3 is a view taken along line 3—3 of FIG. 2A.

DETAILED DESCRIPTION OF THE INVENTION

The process of the invention involves the steps of (1) liquid droplet formation, (2) spheroidization of the droplet (3) freezing of the droplet to form microspheres, (4) irradiation of the frozen microspheres to form latent free radicals, and (5) polymerizing the microspheres while thawing the microspheres to activate the free radicals. Steps (2) and (3) are conducted in a containerless environment. Containerless environment of the invention means a process in which the droplet does not contact the walls of the container. Referring now to FIG. 1, a polymerizable liquid is fed from supply reservoir 10 to the droplet generator 12. A droplet 14 is deployed from outlet 16 of a nozzle 18 into a column 20 of gaseous environment contained within a container 22. As the droplet moves through the column 20, it is formed into a sphere 24 by fluid dynamic forces.

The droplet can be solidified as it passes through the zone 26 surrounded by the cryogenic jacket 30 but preferably the droplets are frozen as they enter the pool of cryogenic liquid 29 in the jacketed collector 28. The falling droplets 31 vaporize the cryogenic liquid to form a layer 33 of vapor. The particles float in the layer 33 and migrate to the grounded edge 35 of the collector and are discharged. The particles fall to the bottom of the collector 28 and pass through the outlet 37 into a Dewar container 39 containing a charge of thawing liquid. The Dewar flask 39 is subjected to ionizing radiation from a radiation source 45 to form latent free radicals within the interior of the microspheres 31. As the liquid 41 thaws, the free radicals are activated to polymerize the microspheres in collector 28.

Containerless spheroidization may be provided during acoustic, aerodynamic or electrostatic forces. Electrostatic levitation is preferred since acoustic or aerodynamic forces are more likely to distort the shape of the liquid droplet. The levitation column can be horizontal or vertical. Horizontal columns can be slightly tilted so that the droplets and hardened particles are pulled toward the outlet of the device by the action of gravity.

Drop generators capable of developing evenly-sized drops is readily available commercially. One type of drop generator is based on Rayleigh instability of a charged fluid. A hollow needle is filled with liquid so that a partial drop protrudes from the end of the needle. Sufficient charge applied to the drop causes the drop to deform into a Taylor cone and to be ejected from the cone. Very small charged droplets of equal size are ejected from the apex of the cone. Control of the size of the tube, the character of the liquid and the amount of charge determines the drop size.

A piezoelectric drop generator could be used similar to those used in cell sorters and ink jet printers. A piezoelectric crystal connected to the back of a small fluid filled cavity having a small opening in front is energized with a voltage pulse. The piezoelectric crystal expands, reducing the cavity volume. A small, constant-size droplet is ejected with each pulse of the crystal. Drops can be made in a size ranging from 1000 Angstroms up to 1000 microns (or a few millimeters).

Since the liquid droplet can be quickly frozen, long residence time in the column is not necessary. The liquid droplet can be spheroidized while in free fall through a gaseous column. Gravity forces do not appear to unduly distort the shape of the droplets before they can be frozen. The process can also be practiced in the zero-gravity environment of deep space. It is also preferred to charge the liquid droplets so that they repel each other and fan out into a cone-shaped pattern as they drop toward the collector.

A preferred apparatus for producing evenly sized polymeric microspheres is illustrated in FIGS. 2A, 2B and 3. The drop generator 100 consisted of a monomer reservoir 102 which was pressurized by a pressure regulated tank 104 of nitrogen gas. The monomer flowed through a pre-filter 106 which was situated before the injection nozzle 108. During "spraying" of the monomer, the reservoir 102 was pressurized with nitrogen gas causing the monomer to be ejected from the nozzle 108. The nozzle 108 was then vibrated by a piezoelectric crystal 110 which was in intimate contact with the nozzle. The piezoelectric crystal was driven by the sinusoidal wave generator 112.

As the stream of monomer was ejected from the vibrated nozzle 108, uniform liquid droplets 114 were formed. The droplets passed through the center 116 of a cylindrical ring deflection electrode 120 to which a high positive potential was applied from the DC source 122. This resulted in a positive charge being impressed on the surface of the droplets. The like charge preventing the droplets 114 from coalescing as they fell to the collection pan 126. The charge also caused the spray of droplets to fan out into a cone shape 128. As the drops 114 fell into the body 130 of liquid nitrogen, they vaporized a portion of the liquid to form a vapor layer 145. The like charge also tended to prevent coalescence of the droplets as they floated in the vapor layer 145 on the surface of the body 130 of liquid nitrogen in the grounded insulated collection vessel 134. The collection vessel included a thermally insulated cylindrical bowl 140 in which was mounted a catch pan 142 having an outlet 144 over the collection pan 126. Prior to spraying the monomer, the bowl 140 was filled with liquid nitrogen from tank 146. As the monomer was sprayed, liquid nitrogen from tank 146 was added to maintain the initial level. The monomer was first sprayed into a closed cover, not shown, placed over the bowl until all the parameters were adjusted properly. After all the parameters were set, and the stream of monomer was breaking "cleanly", the closed cover was removed and the cover 150 with the central opening 103 was placed on the bowl 140 to allow the uniform droplets to collect in the pan 126. If at any time the stream became unstable, or at the end of a run, the closed cove was replaced in order to collect any droplets not uniform in size. The liquid drops 114 in the vaporized layer 145 were mutually repelled toward the pool edge, passed under a ring 148 of a dozen high-voltage-AC-charged needle electrodes 160. The electrodes 160 were corona discharged by the high voltage AC source 149, then vitrified and sank, maintaining their spherical shape. The drops fell through the open center 144 of the inner pan 142 onto the collection pan 126.

After all of the monomer had been sprayed, any particles on the side of the collection bowl were carefully swept off with a nitrogen cooled brush to the bottom of the collector pan 126. The monosized particles 162 were then carefully tranferred into a small Dewar 164. Some of them were then examined under the microscope at this point (in liquid nitrogen) to confirm that they were indeed monosized and had a uniform surface. The Dewar was then placed in a 0.1 Mrad Co60 source 166, and irradiated for the appropriate time.

When the particles were removed from the Co60 source, they were poured into a thawing Dewar with (at least two times their mass of) previously frozen hexane in the bottom (with liquid nitrogen). Excess liquid nitrogen was then added, and the Dewar placed into a minus 28° refrigerator. The internal temperature of the Dewar was monitored by means of a thermocouple.

After the appropriate thawing time, the particles were washed in lower boiling solvent such as ethanol to remove any hexane. They were then boiled in the solvent to extract any residual monomer.

The entire system can readily be automated to allow continuous production of the microspheres. The environment of space also provides a vacuum environment for the column. Inert atmospheres such as vacuum, nitrogen or argon can be provided on land based systems by enclosing the column from the injector inlet to the particle outlet. The like-charged beads repel each other maintaining separation along the axis of the column.

The liquid droplets may be neat, i.e., pure monomer, or may contain vaporizable solvent or diluent such as water or organic solvent usually from 0.1 to 30 percent by weight of solvent or diluent. The monomer is polymerizable by the radiation applied to the frozen microspheres either directly or indirectly by means of a photoinitiator that is activated by the radiation to generate a polymerizing species such as a free radical. Suitable U.V. photoinitiators such as aromatic ketones, suitably 2, 2-dimethoxy-2-phenylacetophenone or 1-hydroxycyclohexophenyl ketone may be present in an amount of 0.1 to 10 percent. The polymerization reaction occurs at higher rates as the amount of photoinitiator is increased.

The droplets may also contain a dispersion of small filler particles such as 0.1 to 60 percent by weight of dense metals or metal oxides. Fluorescent and non-fluorescent dye may also be incorporated with the mixture to prepare colored particles.

The magnetic particles may be blended into the polymerizable liquid from a suspension of the magnetic particles in water or organic liquid. Magnetite suspended in an aqueous liquid containing a surfactant suspending agent is commercially available. Aqueous suspensions of magnetite without surfactants can be made. Other fillers that can be utilized are colloidal iron, cobalt or nickel which are all strongly magnetic. High intensity magnetic fields can be obtained by dispersing samarium-cobalt or neodymium-cobalt magnetic materials in the polymerizable liquid.

Unsaturated compounds, particularly acrylic monomers, polymerize by addition polymerization when subjected to thermal, U.V., gamma or other actinic radiation. Representative hydrophobic acrylic monomers are the acrylate esters such as compounds of the formula:

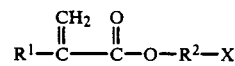

where $R^1$ is hydrogen or lower alkyl of 1-8 carbon atoms, $R^2$ is alkylene of 1 to 12 carbon atoms and X is a hydrophobic group such as lower alkyl or alkoxy of 1 to 8 carbon atoms. Representative acrylate esters are methyl methacrylate, methyl acrylate, ethyl methacrylate or propyl methacrylate.

Hydrophilic and functional microspheres provide biocompatible substrates having surface sites available for covalent bonding. Hydrophilic surface also reduces the non-specific binding of protein on their surface which can cause the denaturing of protein and/or cross reactions. These monomers may be mono-unsaturated compounds containing a functional group such as aldehyde substituted acrylic monomers. Representative monomers are acrolein, acrylamide, methacrylamide, acrylic acid, methacrylic acid, dimethylamino-methacrylate or hydroxy-lower alkyl or amino-lower alkyl acrylates of the formula:

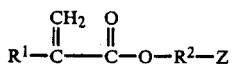

where $R^1$ is hydrogen or lower alkyl of 1–8 carbon atoms, $R^2$ is alkylene of 1–12 carbon atoms, and Z is —OH or $R^3$ or $R^4$ arei ndividually selected from H, lower alkyl, or lower alkoxy of 1–8 carbon atoms. 2-hydroxyethyl methacrylate (HEMA), 3-hydroxypropyl methacrylate and 2-aminoethyl methacrylate are readily available commercially. Porosity and hydrophilicity increase with increasing concentration of monomer.

Inclusion of polyunsaturated compounds also provides cross-linked beads which are less likely to agglomerate. The polyunsaturated compounds are generally present in the monomer mixture in an amount from 0.1 to 20 percent by weight, generally 6 to 12 percent by weight and are suitably a compatible diene or triene polyvinyl compound capable of addition polymerization with the covalent bonding monomer such as ethylene glycol dimethacrylate, trimethylol-propanetrimethacrylate, N,N'-methylene-bis-acrylamide (BIS), hexahydro-1,3,5-triacryloyl-s-triazene or divinyl benzene.

The monomer mixture may contain a large pecentage, suitably from 40 to 70 percent of sparingly water-soluble monomers having hydrophobic characteristics. The cross-linking agent is sometimes sparingly water soluble. Hydrophobic charateristics can also be provided with monomers such as lower alkyl acrylates, suitably methyl methacrylate or ethyl methacrylate or styrene, or a vinyl pyridine. Vinyl pyridines suitable for use in the invention are 2-vinyl pyridine, 4-vinyl pyridine and 2-methyl-5-vinyl pyridine.

The metal or metal compound particles are preferably fine, evenly-sized materials having a uniform diameter smaller than the resultant microsphere diameter, typically below 1000 Angstroms. The metals are preferably the electron dense heavy metals having a high atomic number above 50, preferably above 75 such as Pb, Co, Pt, Au, Fe. The metal may be magnetically attractable such as Fe, Ni, Co or alloys thereof or an inorganic magnetic compound such as a metal oxide. The magnetic material is preferably a magnetic iron oxide of the formula $Fe_3O_4$. Some hard ceramic-type ferrites, such as lithium ferrites can also be used.

Preparation of 155 Micron Poly-HEMA Particles with C.V. of 1.57

3% BIS (by weight) was dissolved in 150 ml of HEMA by means of sonication. This mixture was then filtered two times through a 12 micron filter to remove any particulates which might clog the spraying system. Nitrogen gas was bubbled into the mixture for 15 minutes to remove dissolved oxygen and the mixture was placed into the monomer reservoir. A nozzle with an orifice of diameter 70 micron was placed on the tip of the nozzle and pressure (20 psi) applied to the monomer reservoir. As the stream was ejected from the nozzle, the following parameters were adjusted: (a) the flow rate, (b) the piezoelectric excitation frequency and amplitude, (c) the potential of the deflector electrode, and (d) the frequency of the strobe light. After all the parameters were optimized, the entire contents were sprayed through the system at least two times to ensure the stability of the system.

The following parameters are the final values to produce 155 micron (C.V. of 1.57%) particles: pressure applied to the monomer reservoir 35 psi, flow rate of 1.1 ml/min, piezoelectric vibration frequency of 4.79 kHz, amplitude 150 volts A.C., and 1.5 kV applied to the deflector electrode at a distance of 2 cm from the tip of the nozzle.

The vitrified HEMA particles were collected as described above. They were irradiated with the Co source for 5 hours to give a total dose of 0.5 Mrad. They were then thawed as described above at a rate of approximately 10 degrees per hour.

Preparation of 300 Micron Poly-GMA Particles

The technique for the preparation of poly-GMA particles was similar to the procedure for the preparation of the poly-HEMA particles. However, the viscosity of GMA is much higher than that of HEMA so that the spraying apparatus had to be modified. Any attempts to spray GMA at room temperature with a 70 micron nozzle orifice failed because of its high viscosity, even when sprayed at 125 psi pressure. In order to spray the GMA monomer, two parameters were changed: (a) a 150 micron nozzle orifice was used, and (b) to lower the viscosity of the GMA, a heating tape was wrapped around the nozzle assembly. When the nozzle was heated to 70°, the monomer was sprayable. However, at this elevated temperature, the monomer quickly gelled, clogging the nozzle. In order to spray the GMA at elevated temperature, 3000 p.p.m., hydroquinone had to be added to the purified monomer as a stabilizer. The mixture was then sonicated for approximately 15 minutes while on ice in a bath sonicator.

The inhibited GMA monomer was filtered twice with a 12 micron filter; then nitrogen gas was bubbled into the monomer for 15 minutes to purge it of oxygen. At 70°, the following parameters were used to produce 300 micron poly-GMA particles: The flow rate was 3.3 ml/min, 10 psi was pressure applied to the monomer reservoir, the piezoelectric vibration frequency was 3.88 kHz, and the amplitude 140 volts A.C., and the deflector potential set to 0.78 kilovolts D.C. at a distance of 2 cm from the end of the nozzle.

The vitrified GMA particles were collected as described above and were irradiated as above for a total dosage of 0.6 Mrad. They were then allowed to thaw in a hexane slush as described above at a rate of approximately 10°/hour.

Post Irradiation Cross-linking of the Microspheres

The resulting poly-HEMA and poly-GMA particles tended to swell (up to 20% in diameter) when placed in water or other organic solvents which was undesirable if the particles were to be used as a packing material in affinity chromatography. They were therefore, solvent exchanged into distilled water and re-irradiated for 14 hours each at room temperature as described above.

Preparation of Porous Microspheres

Porous microspheres were prepared by radiation of frozen monomer droplets containing non-polymerizable diluent. Two series of polymerizations were conducted using gamma radiation of frozen monomer. Various monomer, diluent, cross-linking agent mixtures were prepared according to Table 1. The mixture was poured into a vessel and forced through a nozzle by pressurizing the vessel with a nitrogen gas cylinder. The nozzle was mounted on the tip of the diaphram of a loudspeaker which in turn was connected to a frequency generator. By tuning the frequency and the monomer mixture flow rate, a steady stream of monomer droplets was formed. Each of the droplets were identical in size and were collected in liquid nitrogen. The frozen monomer droplets with excess of liquid nitrogen were then irradiated by Cobalt 60 source for 4 hours at about 0.070 MRad/hr. The irradiated droplets were then allowed to thaw very slowly in a −20 degree Celcius freezer. The thawing process took about 20 hours and during these 20 hours, the stored free radicals initiated the polymerization and became microspheres.

TABLE I

| | MONOMER COMPOSITION | | |
|---|---|---|---|
| | HEMA (g) | Diluent (g) | TMPTA (g) |
| A | 35 | 0 | 15 |
| B | 35 | ethyl acetate 10 | 15 |
| C | 35 | ethyl acetate 20 | 15 |
| D | 35 | ethyl acetate 50 | 15 |
| E | 35 | water 10 | 15 |
| F | 35 | water 20 | 15 |
| G | 35 | water 50 | 15 |

The water or ethyl acetate diluent was added to create unreactive holes i.e., the volume occupied by diluent molecules did not incorporate in the polymer matrix. After polymerization was completed, the removal of diluent by evaporation resulted in microholes throughout the particles. The porosity of these microspheres was examined by surface area measurement and by solvent swelling. For surface area determination, all samples were lyopholized and were measured by the nitrogen adsorption. For solvent swelling test, all samples were exchanged to 100% ethanol. The weight difference between microspheres at fully swollen stage and after vacuum dried was used as the swelling capacity which is directly related to the porosity.

All runs resulted in production of uniform microspheres of 300–500 miceons in diameter depending on the flow rate and monomer to diluent ratio.

All swelling capability was measured in 100% ethanol.

| Sample | Wet Weight (g) | Dried Weight (g) | Swollen/Dried |
|---|---|---|---|
| A | 2.29 | 0.58 | 4 |
| B | 2.91 | 0.50 | 5.8 |
| C | 2.56 | 0.36 | 7.1 |
| D | 1.95 | 0.23 | 8.2 |
| E | 2.68 | 0.62 | 4.3 |
| F | 2.49 | 0.52 | 4.8 |
| G | 2.11 | 0.40 | 5.2 |

Apparently, ethyl acetate is a better diluent for preparing porous microspheres. This may be due to the higher miscibility with all ingredients initially and during polymerization.

The containerless spraying and polymerization methods of the invention make large spherical particles more uniform than those of any prior process. The polyHEMA beads produced has a CV of 1.57% at 155 $\mu$. For comparison, commercial latex particles have a CV of 7% at 200 $\mu$. In addition, no seiving is required. Particle size can be easily varied from 50 $\mu$ to 1 mm with similar uniformity.

The methods are not limited to HEMA but can be used with hydrophilic or hydrophobic materials, monomers, polymers, mixtures of polymers and monomers, melted polymers or solution, nitrocellulose, albumin, styrene, waxes, or agarose. Inclusions such as fluorescent dyes or other compounds incoporated into the sprayed mix. Porosity can be controlled by adding non-reaction diluents. Many post-polymerization procedures can thus be eliminated, simplifying production. Large quantities, up to kilograms per day per injector, can be produced. Quick cooling can preserve sphericity, allowing vitrified drops to be polymerized.

It is to be realized that only preferred embodiments of the invention have been described and the numerous substitutions, modifications and alterations are permissible without departing from the spirit and scope of the invention as defined in the following claims.

We claim:

1. A method of forming uniform, polymeric microspheres comprising the steps of:
   injecting a plurality of individual, uniformly sized liquid droplets comprising radiation polymerizable monomer into a zone defined by the walls of a container in a manner in which the droplets do not contact each other or the walls of the container;
   spheroidizing the droplets while in the zone to form uniformly-shaped liquid microspheres;
   freezing the microsphere droplets to convert the droplets into frozen uniformly shaped and sized microspheres;
   radiating the frozen microspheres to form latent free radicals; and
   slowly thawng the frozen microspheres to activate the free radicals and polymerize monomer to form the polymer.

2. A method according to claim 1 in which the liquid droplets are frozen into a non-crystalline, glassy state.

3. A method according to claim 1 in which the injected droplets are charged by passing through an annular electrode.

4. A method according to claim 1 in which the droplets are injected into a vertical zone.

5. A method according to claim 1 in which the droplets are deployed into and levitated within a horizontal zone.

6. A method according to claim 4 in which the frozen microspheres are collected in a vessel containing a pool of cryogenic liquid.

7. A method according to claim 6 in which the frozen microspheres vaporize a portion of the cryogenic liquid to form a vapor layer which suspends the microspheres.

8. A method according to claim 7 in which the suspended, charged microspheres repel each other and move to the outer edge of the layer.

9. A method according to claim 8 further including the step of discharging the microspheres while at the edge of the layer.

10. A method according to claim 9 further including the step of collecting the discharged microspheres and radiating the discharged, frozen microspheres while immersed in cryogenic liquid.

11. A method according to claim 1 in which the radiation polymerizable monomer comprises a mono-unsaturated acrylic monomer.

12. A method according to claim 11 in which the acrylic monomer is selected from the group consisting of acrolein, acrylamide, methacrylamide, acrylic acid, methacrylic acid, dimethylamino-methacrylate or hydroxy-or amino-alkylacrylates of the formula:

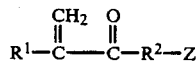

where $R^1$ is H or lower alkyl of 1 to 8 carbon atoms, $R^2$ is alkylene of 1 to 12 carbon atoms and Z is OH or $R^3$-N-$R^4$ where $R^3$ and $R^4$ are individually selected from H, lower alkyl of 1 to 8 carbon atoms or lower alkoxy of 1 to 8 carbon atoms.

13. A method according to claim 12 in which the monomer is hydroxyethylmethacrylate.

14. A method according to claim 12 in which the liquid polymerizable monomer contains 0.1 to 10% of a radiation curable cross-linking agent.

15. An apparatus for forming uniformly shaped and sized, polymeric microspheres comprising in combination:
  means for forming uniformly sized droplets of liquid monomer;
  means for applying a like charge to the droplets;
  means for spheroidizing the droplets to form evenly-shaped microspheres;
  a collection vessel for holding a pool of cryogenic liquid for receiving the evenly-shaped and evenly-sized, charged microspheres and freezing the microspheres to maintain said even size and shape;
  means for discharging the microspheres;
  irradiation means for applying free-radical generating radiation to the frozen microspheres for generating latent free radicals therein; and
  thawing means receiving the frozen microspheres for slowly thawing the microspheres whereby the latent free radicals are activated and polymerize the monomer into uniformly sized and shaped polymeric microspheres.

16. An apparatus according to claim 15 in which the droplet forming means includes a piezoelectric crystal pulsed spray nozzle.

17. An apparatus according to claim 16 in which the charging means includes an annular D.C. electrode positioned below the outlet of the nozzle.

18. An apparatus according to claim 15 in which the charged, frozen microspheres vaporize a portion of the cryogenic liquid to form a vapor layer and the charged microspheres move to the outer edge of the layer and the discharge means comprises a plurality of electrodes positioned along the periphery of the collection vessel adjacent said layer.

19. An apparatus according to claim 18 in which the collection vessel includes a cover having a central aperture for passage of the frozen microspheres.

20. An apparatus according to claim 19 in which the discharge electrodes are mounted on said cover.

* * * * *